United States Patent [19]
Hodosh

[11] Patent Number: 6,099,868
[45] Date of Patent: Aug. 8, 2000

[54] METHOD OF USING POTASSIUM NITRATE FOR PAIN REDUCTION

[76] Inventor: Milton Hodosh, 243 Elmwood Ave., Providence, R.I. 02907

[21] Appl. No.: 09/439,858

[22] Filed: Nov. 12, 1999

[51] Int. Cl.[7] .......................... A61K 33/00; A61K 31/34; A61K 31/24; A61K 31/19; A61K 31/195
[52] U.S. Cl. ..................... 424/600; 514/470; 514/535; 514/557; 514/561
[58] Field of Search ............................ 424/600; 514/470, 514/535, 557, 561

[56] References Cited

U.S. PATENT DOCUMENTS

| | | |
|---|---|---|
| 3,863,006 | 1/1975 | Hodosh . |
| 4,060,600 | 11/1977 | Vit . |
| 4,191,750 | 3/1980 | Hodosh . |
| 4,343,608 | 8/1982 | Hodosh . |
| 4,400,373 | 8/1983 | Hodosh . |
| 4,407,675 | 10/1983 | Hodosh . |
| 4,961,923 | 10/1990 | Heyde . |
| 5,032,388 | 7/1991 | Tikkanen . |
| 5,120,460 | 6/1992 | Asai et al. . |
| 5,139,768 | 8/1992 | Friedman . |
| 5,147,632 | 9/1992 | Pan et al. . |
| 5,153,006 | 10/1992 | Hodosh . |
| 5,374,417 | 12/1994 | Norfleet et al. . |
| 5,403,577 | 4/1995 | Friedman . |
| 5,522,726 | 6/1996 | Hodosh . |

*Primary Examiner*—Raymond Henley, III
*Attorney, Agent, or Firm*—Salter & Michaelson

[57] ABSTRACT

A method of anesthetizing a tooth requiring tooth preparation, caries removal or manual manipulation thereof is disclosed. The method includes the steps of applying a composition having a high concentration of potassium to the tooth requiring tooth preparation, caries removal or manual manipulation, the composition being adapted to anesthetize the tooth so that the tooth may be drilled or manually manipulated, whereby the potassium enters the dentinal tubules and odontoblastic fibrils and penetrates the pulpal tissues of the tooth for anesthetizing the tooth. The improvement consists essentially of applying a solution of EDTA, EGTA, and citric acid to the tooth before the application of the potassium composition, the solution of EDTA, EGTA, and citric acid effectively removing a smear layer from the tooth so as to facilitate the penetration of the potassium solution through the dentinal tubules and odontoblastic fibrils.

8 Claims, No Drawings

METHOD OF USING POTASSIUM NITRATE FOR PAIN REDUCTION

BACKGROUND OF THE INVENTION

1. Field of the Invention

The present invention relates to the treatment of pain and more particularly to a method for using potassium nitrate to reduce pain associated with dental and oral procedures.

2. Background and Summary of the Invention

The inventor of the present invention has done extensive research into the cause of pain, particularly in the area of oral and dental surgery. In this research, it has been discovered that potassium is effective for desensitizing hypersensitive teeth (U.S. Pat. No. 3,863,006), for treating canker sores (U.S. Pat. No. 4,191,750), for preserving dental pulp (U.S. Pat. Nos. 4,343,608 and 4,407,675) for treating gingival and periodontal tissues (U.S. Pat. No. 4,400373), for treating post-restoration dental pain (U.S. Pat. No. 5,153,006 and for anesthetizing teeth (U.S. Pat. No. 5,522,726), all of which patents are incorporated herein by reference.

Accordingly, the present invention is a result of the continued research of the inventor, which research has determined that potassium nitrate, in combination with other compounds, can be used for the reduction of pain associated with a variety of procedures and conditions. Accordingly, the present invention includes the combination of potassium nitrate and dimethyl isosorbide, for the treatment of ulcerative lesions of the skin and mucous membranes, for improved tooth desensitization of hypersensitive teeth, the use of potassium nitrate, EGTA, citric acid, and EDTA, wherein the EDTA, EGTA, citric acid, etc. removes the smear layer from the teeth first to allow the potassium nitrate next to better penetrate to the nerves of the tooth, as set forth in the '726 patent, and the combination of potassium nitrate and various potent topical anesthetics to simultaneously anesthetize the a tooth and the surrounding gum tissue to provide pain-free periodontal and hygienist scaling and maintenance visits. This same combination of substances can be applied locally for effective post-operative and restorative pain control, post-periodontal and other post-surgery comfort while healing is taking place. This diminishes the need to use ingested and/or injected analgesics or narcotics for pain control.

According to a first embodiment of the invention, a method of anesthetizing a tooth requiring tooth preparation, caries removal or manual manipulation thereof is disclosed. The method comprises the step of applying a composition having a high concentration of potassium to the tooth requiring tooth preparation, caries removal or manual manipulation, the composition being adapted to anesthetize the tooth so that the tooth may be drilled or manually manipulated, whereby the potassium enters the dentinal tubules and odontoblastic fibrils and penetrates the pulpal tissues of the tooth for anesthetizing the tooth. The improvement consists essentially of applying a solution of EDTA, EGTA, and citric acid to the tooth before the application of the potassium composition, the solution of EDTA. EGTA, and citric acid effectively and safely removing a smear layer from the tooth so as to facilitate the penetration of the potassium solution through the dentinal tubules and odontoblastic fibrils.

According to another embodiment of the invention, a method of anesthetizing a tooth requiring tooth preparation, caries removal or manual manipulation thereof is disclosed. The method comprises the step of applying a composition having a high concentration of potassium to the tooth requiring tooth preparation, caries removal or manual manipulation, the composition being adapted to anesthetize the tooth so that the tooth may be drilled or manually manipulated, whereby the potassium enters the dentinal tubules and odontoblastic fibrils and penetrates the pulpal tissues of the tooth for anesthetizing the tooth. The improvement consists essentially of including a topical anesthetic in the potassium solution to enable the solution to anesthetize the tooth and the gingivae and other soft tissues surrounding the tooth.

According to yet another embodiment of the invention, a method of anesthetizing a tooth requiring tooth preparation, caries removal or manual manipulation thereof is disclosed. The method comprises the step of applying a composition having a high concentration of potassium to the tooth requiring tooth preparation, caries removal or manual manipulation, the composition being adapted to anesthetize the tooth so that the tooth may be drilled or manually manipulated, whereby the potassium enters the dentinal tubules and odontoblastic fibrils and penetrates the pulpal tissues of the tooth for anesthetizing the tooth. The improvement consists essentially of including a concentration of dimethyl isosorbide in the potassium solution, whereby the concentration of dimethyl isosorbide acts to increase the ability of the potassium to penetrate in increased amounts through the dentinal tubules and odontoblastic fibrils and to better penetrate the pulpal tissues of the tooth for anesthetizing the tooth.

By employing an enhancer, such as Dimethyl Isosorbide or phospholipids, we are able to improve the desensitizing of hypersensitive teeth, since Dimethyl Isosorbide enhances the penetration of potassium ions (whatever the source of potassium-refer to U.S. Pat. No. 5,522,726) through the tooth and dentinal tubules into the pulpal tissues. The effect is to provide faster, more complete, longer lasting (duration) desensitization. Another application is to use potent topical anesthetics in combination with high concentration potassium compounds (e.g., potassium nitrate, potassium citrate, potassium chloride-refer to U.S. Pat. No. 5,522,726) for providing pain-free comfort during periodontal and/or hygienist scaling, maintenance, and other manipulative procedures. We use saturated $KNO_3$, 20 percent benzocaine, 10 percent tetracaine for controlling both tooth and gingival pain. It controls pain with such hygienic procedures, periodontal treatments, papillectomy. Since the gingival and other soft oral tissues do not have dentinal tubules, the soft tissue anesthesia is accomplished by potent topical anesthetics. Some are benadryl, lidocaine, tetracaine, benzocaine, cetracaine, etc.

According to yet another embodiment of the invention, a method for reducing pain and shortening the healing period of in aphthous ulcers is disclosed. The method includes the step of applying a solution of potassium (2 percent–35 percent) and dimethyl isosorbide to the site of the ulcer, whereby the solution acts on nerve endings within the ulcer to reduce inflammation and prevent the induction of pain within the ulcer while promoting faster healing of the ulcer. Dimethyl isosorbide enhances the effect of the potassium ion by aiding its penetration into the affected tissue. Any source of potassium can be utilized for this purpose. Examples are $KNO_3$, $KCl$, $KCO_3$, $KPO_4$, etc. (refer to issued U.S. Pat. No. 5,522,726). This is an improvement over the use of potassium nitrate to treat canker sores (U.S. Pat. No. 4,191,750).

DETAILED DESCRIPTION

In general, human nerve cells have a low threshold of excitation. Stimuli for exciting nerve cells may be electrical, chemical, or mechanical. A stimulus creates a physicochemical disturbance or impulse which is transmitted by conduction along the nerve axon to its termination. Nerves do not transmit impulse passively (as do telephone wires) and conduction of nerve impulses, although rapid, is much slower than that of electricity. Conduction is an active self-propagating process which requires expenditure of energy by the nerve at a constant amplitude and velocity.

For more than one hundred years it has been known that there are electrical potential changes in a nerve when it conducts impulses. There is a constant potential difference between the inside and the outside of the nerve cell at rest. The magnitude of this potential in most neurons (otherwise referred to as "Resting Membrane Potential") is approximately seventy-eight millivolts (MV) and is expressed as a negative potential (i.e.,-70-80 MV) because the inside of the cell is negatively charged relative to the positively charged exterior of the cell. If the nerve axon is stimulated and a conducted impulse occurs, a characteristic series of potential changes is observed.

The first manifestation of the approaching impulse is a beginning depolarization of the membrane. The potential changes are small, being measured in millivolts. After an initial fifteen millivolts of depolarization of the membrane, the rate of depolarization increases. The point at which this change in rate occurs is termed the "firing level". Thereafter it rapidly reaches and overshoots the iso-potential (zero potential) line to approximately thirty-five millivolts positive. It then reverses and falls rapidly towards a resting level. When re-polarization is about seventy percent completed, the rate of re-polarization decreases approaching the resting level more slowly. The sharp rise and rapid fall are the spike potential of the nerve axon, and the slower fall at the end of the process is the after-depolarization. The whole sequence of potential changes is called the "action potential". Once the minimal intensity of stimulating current (threshold intensity which will just produce an impulse) is reached, a full fledged action potential is produced.

Further increases in the intensity of a stimulus produce no increment or other change in the action potential. The action potential fails to occur if the stimulus is subthreshold in magnitude, and it occurs with a constant amplitude and form regardless of the strength of the stimulus if the stimulus is at or above the threshold intensity. The action potential is therefore all or none. The depolarizing forces must be stronger than the re-polarizing forces in order to overwhelm the re-polarizing process (i.e., fifteen millivolts) and an action potential results. At this level of depolarization some fundamental change in the nerve leads to runaway depolarization in the membrane.

At rest, the nerve cell membrane is polarized with positive charges lined up along the outside of the membrane and negative charges along the inside of the membrane. During the action potential this polarity is abolished and for a brief period of time it is actually reversed. Positive charges from the membrane ahead of and behind the action potential flow into the area of negativity. By drawing off positive charges, this flow decreases the polarity of the membrane ahead of the action potential. Electronic depolarization initiates a local response, and when the firing level is reached a propagated response occurs which in turn electronically depolarizes the membrane in front of it. This sequence of events moves regularly along an unmyelinated nerve axon (i.e., a nerve axon lacking a myelin sheath) to its end. The self-propagating nature of the nerve impulse is due to circular current flow and successive electronic depolarization to the fire level of the membrane ahead of the axon potential. Once initiated, a mixing impulse does not depolarize the area behind it to the firing level because the area is refractory.

The action potentials produced at synaptic junctions also depend on electronic depolarization of the nerve cell membrane to the firing level. Conduction in myelinated axons depends on a similar pattern of current flow, but myelin is a relative effective insulator, and current flow through it is negligible. Instead, depolarization in myelinated axons jumps from one node of Ranvier to the next, with the current sink at the active node serving to electronically depolarize to the firing level. The jumping of depolarization from node to node is called saltatory conduction. Myelinated axons conduct up to fifty times faster than unmyelinated axons.

The innervation of the tooth pulp includes both afferent neurons which conduct sensory impulses, and autonomic fibers which provide neurogenic modulation of the microcirculatory system and perhaps regulate dentinogenesis as well. Most of the nerves of the pulp fall into two categories: A fibers and C fibers. The A fibers are myelinated and the C fibers are unmyelinated. In addition to sensory nerves, sympathetic fibers from the cervical sympathetic ganglion appear with blood vessels. All of the fibers enter the tooth through the apical foramen. The A fibers are enclosed within sheath formed by the Schwann cells. The myelinated A fibers are grouped in bundles in the central region of the apical pulp. Most of the unmyelinated C fibers entering the pulp are located with the fiber bundles in the central region of the apical pulp and are situated toward the periphery of the pulp. Approximately eighty percent of the nerves of the pulp are C fibers. The nerves from the coronal pulp divide and send branches towards the peripheral pulp where a parietal layer of both myelinated and unmyelinated nerve axon form the plexus of Raschkow beneath the cell rich zone. The A fibers of the parietal layer emerge from their myelin sheaths and Schwann cell coverings to ramify into eight to ten unmyelinated branches forming a network under the dentin. Terminal axons exit their Schwann cell investiture and pass between the odontoblast with some fibers actually entering the dentinal tubules lying in close association with the odontoblastic processes.

A nerve axon can conduct in either direction. If an action potential is initiated in the middle of the axon, two impulses traveling in opposite directions are set up by electronic depolarization on either side of the current sink. In humans, impulses normally pass from synaptic junction or receptors along axons to their termination. Such conduction is called "orthodromic" and conduction in the opposite direction is called "antidromic". Synapses, unlike axons, permit conduction in one direction only.

It has been discovered that a tooth subject to hypersensitivity can be desensitized by applying a composition saturated with a potassium containing compound thereto. It has been further discovered that highly concentrated potassium ions and cations, when exposed to the dentinal tubules and odontoblastic processes, penetrate the pulpal tissues of the tooth for desensitizing the tooth. When applied to the tooth, potassium polarizes the pulpal nervous tissues of the tooth thereby rendering these sensory nerves inactive and unable to depolarize for a significant time period until the potassium dissipates. This process, sometimes referred to as "hyperpolarization", allows no stimulus, no matter how strong, to excite the pulpal nervous tissue.

More specifically, in nerve cells, as in other tissues, sodium is actively transported out of the cell and a small amount of potassium is actively transported into the cell.

Potassium diffuses back out of the cell down its concentration gradient, and sodium diffuses back into the cell; however, since the permeability of the membrane to potassium is much greater than it is to sodium at rest, the passive potassium efflux is much greater than the passive sodium influx. Since the membrane is impermeable to most of the anions in the cell, the potassium efflux is not accompanied by an equal flux of anions and the membrane is maintained in a polarized state with the outside of the membrane being positive and the inside of the membrane being negative.

A slight decrease in resting membrane potential leads to increased movement of potassium out of and chlorine into the cell, thereby restoring the resting membrane potential. In the case of nerve cells, there is a unique change in the cell membrane when depolarization exceeds seven millivolts. This change is a voltage dependent increase in membrane permeability to sodium so that the closer the membrane potential is to the firing level the greater the sodium permeability. The electrical and concentration gradients for sodium are both directed inwardly. During a typical injected local response, sodium permeability is slightly increased, but potassium efflux is able to restore the potential to the resting value. When the firing level is reached, permeability is significant enough so that sodium influx further lowers membrane potential and sodium permeability is further increased.

The consequent sodium influx swamps the re-polarizing processes, and runaway depolarization results, producing the spike potential. With the increase in sodium permeability at the start of the action potential, the membrane potential approaches sixty millivolts positive. The membrane potential fails to reach this mark; primarily because the change in sodium permeability is short lived. Sodium permeability starts to return to the resting value during the rising phase of spike potential and sodium conductance is decreased during re-polarization. Additionally, the direction of the electrical gradient for sodium is reversed during the overshoot because the membrane potential is reversed. These factors limit sodium influx and help bring about re-polarization.

Another important factor producing re-polarization of the nerve membrane is the increase in potassium permeability that accompanies sodium permeability. The change in potassium permeability starts more slowly and reaches a peak during the falling phase of the action potential. The increase in permeability decreases the barrier to potassium diffusion, and potassium consequently leaves the cell. The resulting net transfer of positive charge out of the cell serves to complete re-polarization.

The changes in sodium and potassium conductance of an ion is the reciprocal of its electrical resistance in a membrane and is a measure of membrane permeability to that ion. The ionic hypothesis as the basis of action potential is provided by the observation that decreasing the external sodium concentration decreases the size of the action potential, but has little effect on the resting membrane potential since the permeability of the membrane to sodium is very low. Conversely, increasing the external potassium in the tooth, decreases the resting membrane potential. This renders the nerve unable to develop an action potential, and causes the nerve to fail to fire when stimulated.

In this way the potassium applied to the tooth desensitizes the tooth directly in that potassium flows through the vast network of dentinal tubules. The potassium traverses the 30,000–59,000 dentinal tubules per square millimeter of dentin and flows over and through the dentinal tubules and odontoblastic fibrils to the odontoblast and into the pulp increasing the external potassium about the nerve. This interruption of neuron function is caused by the actual bathing of nerve tissue with an abundant source of potassium. This process of hyperpolarizing elevates the membrane potentials as they would be in the absolute refractory period allowing no stimulus, no matter how strong, to excite the nerve. As the potassium bathing the nerve dissipates, the membrane threshold is again decreased as it would be after repolarization. At this point, the patient may begin to feel some pain and concentrated potassium gel is applied again in order to re-anesthetize the tooth and eliminate pain caused by the drill etc.

In cavity preparation, it is important to adhere to basic principles when using a drill, i.e, minimize heat production, use copious water spray to avoid overheating the pulp, and use a light, painting, or wiping motion when drilling. These techniques lessen the feeling in the tooth experienced by the patient. This is important especially as the clinician enters and passes through the enamel to reach the dentinal tubules. When the dentinal tubules are reached, the selected potassium composition is reapplied. This allows the potassium composition to enter into the exposed dentinal tubules.

The potassium composition of the subject invention may be in the form of a liquid, although for greater efficacy the composition preferably comprises a viscous liquid composition, such as a gel. Ointments, pastes and creams have also proven to be very acceptable. In order to properly apply the composition, a liberal amount of it should be applied to the patient's teeth which are subject to hypersensitivity. Preferably, the composition is applied over the tooth for a time period of greater than one minute, at least twice a day, every day. When in the form of a gel, the composition can be applied with a cotton swab or the like. When in the form of a paste, the composition can be brushed onto the patient's teeth with a toothbrush.

As previously stated, the composition comprising potassium is preferable in a viscous form, such as a liquid gel or paste, so that when applied liberally to the tooth, the composition tends to remain in place and is not washed away quickly. It has been found that a viscous liquid gel or paste composition comprising a compound of potassium nitrate at saturation level is especially effective in achieving the objectives of this invention. Contrary to the teachings of the above-noted Pat. No. 3,863,006, it should be pointed out that the potassium containing compound should exceed twenty percent by weight of the overall composition. Preferably, in order to reach saturation level, the composition comprises approximately 35 percent (35%) by weight potassium nitrate and 65 percent (65%) by weight hydroxyethylcellulose and water. Compositions comprising compounds other than potassium nitrate may also be applied; such compounds include potassium bicarbonate, potassium biphthalate, potassium bromide, potassium chromate, potassium acetate, potassium dichromate, potassium phosphate, potassium sulfate, potassium chromium sulfate, potassium citrate, potassium thiocyanate, potassium alum, potassium bitartrate, potassium bromate, potassium carbonate, potassium chlorate, potassium chloroglatinate, potassium chloride, potassium hydroxide, potassium perchlorate, potassium persulfate, potassium oxalate, potassium azide, potassium bromate, potassium fluoride, potassium hydrogen sulfate, potassium iodate, potassium sodium tartrate, etc. However, it has been determined that potassium nitrate produces the best result.

Further experimentation has shown that substances on the tooth can reduce the effectiveness of the potassium solution. These substances include the smear layer of the tooth, which consists of organic and inorganic materials including heat coagulated proteins such as gelatin, which are derived from heat denaturation of collagen under the effects of cutting temperatures. The smear layer may also include saliva, blood and microorganisms.

In order to remove the smear layer before the application of the potassium nitrate anesthetic, a solution of 50% EDTA disodium salt solution 0.02 normal and 50% citric acid is applied to the cemento-enamel junction of the tooth and to other areas of the dentin as tooth preparation and caries removal progresses. The EDTA/citric acid solution effectively removes the smear layer mucopolysaccaride coating and peritubular dentin, thereby exposing the orifices of the dentinal tubules for better penetration of the potassium ions.

With this preparation, the potassium ions enter the exposed dentinal tubules more readily and mingle with their contained fluid (lymph) which occupies about 22% of the tooth's fluid volume flowing through the tubules over the odontoplastic processes and inward to the pulpal nerves, thereby anesthetizing the tooth by this direct path. The solution may also be added to the enamel of the tooth to increase the porosity of the tooth, thereby allowing the potassium ions to penetrate through the enamel into the underlying dentin more readily.

Other smear layer-removing substances that may be used include other acids such as ascorbic acid, phosphoric and lactic acid, gluconic acid salt, polyacrylic acid, tartoric acid, acetic acid, hydrochloric acid, ethylene glycol Bis (2-aminoethyl ether) tetracetic acid (ETGA), and edtate sodium. Smear layers are also removed by sodium hypochlorate with sodium hydroxide or EDTA, formulation based phenol sulfonate, aqueous hydrohide peroxide, and other compounds known in the art.

Another embodiment of the invention includes the addition of a topical anesthetic, such as benzocaine, tetracaine, lidocaine benadryl, etc., with the potassium solution. This solution effectively anesthetizes the tooth and the gingivae or other soft tissues surrounding the tooth. The potassium solution provides direct pulpal anesthesia, as described above. Since the gingivae and other soft oral tissues do not have dentinal tubule which could allow potassium ions to enter their structure as do teeth, the topical anesthetics are combined with the potassium solution to topically anesthetize the tooth's pulp. This combination provides excellent pain control for periodontal and hygienist procedures for treatment and maintenance visits.

A preferred solution includes the following approximate concentrations of elements:

| | |
|---|---|
| Potassium Nitrate | 35% by wt. |
| Benzocaine | 20% by wt. |
| Tetracaine | 10% by wt. |
| Hydroethylcellulose | 15% by wt. |
| Water | 15% by wt. |
| Dimethyl Isosorbate | 10 drops per oz. of the total solution |

It will be understood, however, that other known topical anesthetics may be substituted for the benzocaine and tetracaine in the above solution. Suitable topical anesthetics include lidocaine, phenol benadryl, cetracaine, and others known in the art.

According to another embodiment of the invention, it has been found that, while potassium ions are an excellent anesthetic for use on teeth, which have dentinal tubules for transporting the potassium ions to the nerves of the teeth, it is not as effective as an anesthetic for other tissues of the body. Since these other tissues do not have the tubules which transport the potassium ions to the nerves, another means for transporting the potassium ions to the nerves of the tissue must be used. The skin serves as a protective barrier which limits ionic penetration elements. Therefore, an enhancer is required to bring the potassium ions in quantity to the desired tissue site. The rationale for nerve inactivation is the same wherever nerves are involved. If skin, mucous membranes, muscles, tendons and other tissues can be penetrated by a high gradient of potassium ions which can be brought to surround the nerves in sufficient quantities, then the action potential can be inhibited.

In connection with this, it has been discovered that dimethyl isosorbide is an excellent enhancer of potassium ions for the purpose of delivering the potassium ions to the nerves of the treatment site. The dimethyl isosorbide is mixed as a gel solution which preferably includes the following:

| | |
|---|---|
| Potassium Nitrate | 3.4% by wt. |
| Hydroethylcellulose | 3.4% by wt. |
| dimethyl isosorbide | 1.9% by wt. |
| water | 91% by wt. |

This solution has been found to be effective for the reduction of pain associated with aphthous ulcers (canker sores) and other ulcer-producing illnesses, such as herpes and shingles. Furthermore, the solution has been found effective in the reduction of inflammation associated with inflammatory lesions and localized injuries. When the gel solution is applied to the area to be treated, the dimethyl isosorbide facilitates the penetration of the potassium ions to the nerves which are being stimulated and are therefore causing the patient pain. It has been found that the potassium ions not only exert their pain-inhibiting effects on central nervous system nerves, they also have a remarkable effect on the autonomic nerves by minimizing inflammatory stimulation. Accordingly, the dimethyl isosorbide/$KNO_3$ solution can be used as a pain reducer and anti-inflammatory agent.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. In a method of anesthetizing a tooth requiring tooth preparation, caries removal or manual manipulation thereof, said method comprising the step of applying a composition having a high concentration of potassium to said tooth, the composition being adapted to anesthetize the tooth so that the tooth may be drilled or manually manipulated, whereby said potassium enters the dentinal tubules and odontoblastic fibrils and penetrates the pulpal tissues of the tooth for anesthetizing the tooth, the improvement consisting essentially of applying a solution comprising EDTA, EGTA, or citric acid to the tooth before the application of the potassium composition, said solution effectively removing any smear layer that may exist on the tooth so as to facilitate the penetration of the potassium composition through the enamel, dentinal tubules and odontoblastic fibrils.

2. In a method of anesthetizing a tooth requiring tooth preparation, caries removal or manual manipulation thereof, said method comprising the step of applying a composition having a high concentration of potassium to said tooth, the composition being adapted to anesthetize the tooth so that the tooth may be drilled or manually manipulated, whereby said potassium enters the dentinal tubules and odontoblastic fibrils and penetrates the pulpal tissues of the tooth for anesthetizing the tooth, the improvement consisting essentially of combining a topical anesthetic with the potassium composition to enable the composition to anesthetize the tooth and the gingivae and other soft tissues surrounding the tooth for pain control during post surgical, periodontal, and hygienist procedures.

3. In a method of anesthetizing a tooth requiring tooth preparation, caries removal or manual manipulation thereof, said method comprising the step of applying a composition having a high concentration of potassium to said tooth, the composition being adapted to anesthetize the tooth so that the tooth may be drilled or manually manipulated, whereby said potassium enters the dentinal tubules and odontoblastic fibrils and penetrates the pulpal tissues of the tooth for anesthetizing the tooth, the improvement consisting essentially of combining a concentration of dimethyl isosorbide with the potassium composition, whereby said concentration of dimethyl isosorbide acts to increase the penetration of the potassium through the dentinal tubules and odontoblastic fibrils so as to achieve better penetration of the pulpal tissues of the tooth for more effective anesthetization of the tooth.

4. The method of claim 3 used for the desensitizing of hypersensitive teeth.

5. A method for reducing pain in ulcers comprising the step of applying a solution comprising potassium and dimethyl isosorbide to the site of the ulcer, whereby said solution acts on nerve endings within the ulcer to prevent the induction of pain and inflammation within the ulcer and to diminish the inflammatory response and thus promote faster, better healing.

6. The method of claim 5, wherein said solution comprises concentrated potassium nitrate, dimethyl isosorbide, benzocaine, and tetracaine.

7. A method for treating inflammation that may exist anywhere on the body of a living being comprising the steps of applying a solution comprising potassium and dimethyl isosorbide to the site of the inflammation, whereby said solution prevents the induction of pain within the inflammation, and diminishes the inflammatory response to promote faster, better, healing.

8. The method of claim 7, wherein said solution comprises concentrated potassium nitrate, dimethyl isosorbide, benzocaine and tetracaine.

* * * * *